(12) United States Patent
Van Herpen et al.

(10) Patent No.: US 9,057,492 B2
(45) Date of Patent: Jun. 16, 2015

(54) SURGICAL LAMP FOR BROADBAND AND NARROWBAND ILLUMINATION

(75) Inventors: Maarten Marinus Johannes Wilhelmus Van Herpen, Eindhoven (NL); Robert-Paul Mario Beretty, Eindhoven (NL); Marcellinus Petrus Carolus Michael Krijn, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 19 days.

(21) Appl. No.: 13/816,953

(22) PCT Filed: Aug. 11, 2011

(86) PCT No.: PCT/IB2011/053579
§ 371 (c)(1),
(2), (4) Date: Feb. 14, 2013

(87) PCT Pub. No.: WO2012/023090
PCT Pub. Date: Feb. 23, 2012

(65) Prior Publication Data
US 2013/0147400 A1 Jun. 13, 2013

(30) Foreign Application Priority Data
Aug. 17, 2010 (EP) .................................. 10172995

(51) Int. Cl.
*A61B 1/06* (2006.01)
*F21S 8/00* (2006.01)
(Continued)

(52) U.S. Cl.
CPC ............... *F21S 8/00* (2013.01); *A61B 19/5202* (2013.01); *F21V 23/04* (2013.01); *F21W 2131/205* (2013.01); *F21Y 2101/02* (2013.01); *F21Y 2113/005* (2013.01); *H05B 37/02* (2013.01)

(58) Field of Classification Search
USPC .......... 600/249; 362/147, 227, 230, 231, 234, 362/228, 249.01, 249.02, 257, 259, 260, 362/293, 362, 370, 804
See application file for complete search history.

(56) References Cited

U.S. PATENT DOCUMENTS 4,288,844 A * 9/1981 Fisher et al. ..................... 362/33
5,861,706 A * 1/1999 Lapatovich et al. .......... 313/113
(Continued)

FOREIGN PATENT DOCUMENTS

| EP | 2314246 | 4/2011 |
| EP | 2314247 A1 | 4/2011 |

(Continued)

OTHER PUBLICATIONS

Cyhongquing Tianhai Medical Equipment Co., Ltd., Chongquing, China, disclosed Jun. 16, 2010 on the internet webpage http:/www.alibaba.com/product-gs/271424024/Color_Temperature_Adjustable_Led_Surgical_Light.html.

(Continued)

*Primary Examiner* — Thuy Vinh Tran (57) ABSTRACT

The present invention relates to a surgical lamp (100) comprising both a first light source (110) and a second light source (112), where the first light source is capable of emitting light across a broad first spectral range and the second light source being capable of emitting light having an emission peak in a narrow second spectral range. The surgical lamp further features a light source selecting device (120), capable of selectively turning on and off the first and the second light source. The first light source has a high color rendering index so as to enable objects, such as tissues, to appear in their true color, and the second light source has a low or non-definable color rendering index, so as enable accentuation of particular tissues.

12 Claims, 5 Drawing Sheets

(51) Int. Cl.
*A61B 19/00* (2006.01)
*F21V 23/04* (2006.01)
*H05B 37/02* (2006.01)
*F21W 131/205* (2006.01)
*F21Y 101/02* (2006.01)
*F21Y 113/00* (2006.01)

(56) References Cited

U.S. PATENT DOCUMENTS

| | | |
|---|---|---|
| 6,513,962 B1 * | 2/2003 | Mayshack et al. ............ 362/583 |
| 7,704,206 B2 | 4/2010 | Suzuki |
| 8,292,804 B2 * | 10/2012 | Marka et al. .................. 600/249 |
| 2004/0257007 A1 | 12/2004 | Lys et al. |
| 2005/0046937 A1 | 3/2005 | Sander |
| 2005/0194876 A1 | 9/2005 | Shimada et al. |
| 2006/0109650 A1 | 5/2006 | Hunerbein |
| 2007/0097702 A1 | 5/2007 | Crowder |
| 2008/0285820 A1 | 11/2008 | Voelker |
| 2009/0306478 A1 | 12/2009 | Mizuyoshi |
| 2009/0318771 A1 * | 12/2009 | Marka et al. .................. 600/249 |
| 2010/0039507 A1 | 2/2010 | Imade |
| 2012/0170302 A1 * | 7/2012 | Swayne et al. ................ 362/555 |

FOREIGN PATENT DOCUMENTS

| WO | WO2010007785 | 1/2010 |
|---|---|---|
| WO | 2010027493 A2 | 3/2010 |

OTHER PUBLICATIONS

Palmer, Gregory M. et al "Comparison of Multiexcitation Fluorescence and Diffuse Reflectance Spectroscopy for the Diagnosis of Breast Cancer", IEEE Transactions on Biomedical Engineering, vol. 50, No. 11, Nov. 2003.

* cited by examiner

SURGICAL LAMP FOR BROADBAND AND NARROWBAND ILLUMINATION

FIELD OF THE INVENTION

The present invention relates to a lamp, in particular the present invention relates to a surgical lamp, use of a surgical lamp, and a corresponding method applicable for discriminating between tissues.

BACKGROUND OF THE INVENTION

A surgical lamp may be utilized for illuminating an area which may be subject to surgery. Advantageously, a surgical lamp should enable the human eye to clearly observe illuminated tissues and discriminate between different illuminated tissues.

An LED Surgical light (Model: LCSSL-2203, from the company: Chongqing Tianhai Medical Equipment Co., Ltd, Chongqing, China, disclosed Jun. 16, 2010 on the internet webpage http://www.alibaba.com/productgs/271424024/Color_Temperature_Adjustable_LED_Surgical_Light.html) has been described which enable separate adjustment of brightness and color temperature, and where the color temperature is able to meet kinds of color development for different tissues, improving the clearness degree among fresh, obsolete and necrosis tissues.

However, there may still be a problem that the human eye may not be able to clearly observe illuminated tissues and discriminate between different illuminated tissues.

Hence, an improved surgical lamp would be advantageous, and in particular a more efficient and/or reliable surgical lamp would be advantageous.

SUMMARY OF THE INVENTION

In particular, it may be seen as an object of the present invention to provide a surgical lamp that solves the above mentioned problem and which enables the human eye to more clearly observe illuminated tissues and discriminate between different illuminated tissues.

It is a further object of the present invention to provide an alternative to the prior art.

Thus, the above described object and several other objects are intended to be obtained in a first aspect of the invention by providing a surgical lamp comprising a first light source, the first light source being capable of emitting light across a first spectral range, and a second light source, the second light source being capable of emitting light having an emission peak, which emission peak has a width corresponding to a second spectral range, wherein the second spectral range is a narrow spectral range with respect to the first spectral range and wherein the first light source has a definable first color rendering index and the second light source has a definable second color rendering index being lower that the first color rendering index or the second light source has a second color rendering index being non-definable, the surgical lamp further comprising a light source selecting device, where the light source selecting device is capable of selectively switching the first light source on and off and further capable of selectively switching the second light source on and off.

The invention is particularly, but not exclusively, advantageous for illuminating certain objects, such as animal tissue so as to enable a human observer to discriminate between different objects, such as different animal tissues. The light emitted from the first light source has a high color rendering index so that colors of the objects are perceived as the true colors, or at least relatively close to the true colors. The light emitted from the second light source has a lower or non-definable color rendering index so that specific objects, such as a specific animal tissue, may stand out visually since the optical properties for that particular object may stand out, from other objects, in the second spectral range.

Diffuse reflectance spectroscopy may be used to distinguish between different tissues, such as normal, benign and cancerous tissues, by comparing the average amplitudes of diffuse light. For example, the wavelength at 260 nm is indicative of nucleic acid levels, 280 nm is indicative of protein levels, 420 nm is indicative of Soret band hemoglobin levels, 480 nm is indicative of beta-carotene levels, and 550 nm is indicative of Q-band hemoglobin levels. In this way, and when using visible wavelengths, a human eye, such as the human eye of a physician, may more clearly be able to see the difference between cancerous tissue and other tissues, thereby seeing what tissue to remove. However, human eyes cannot distinguish these optical effects very well because the human eye sees a wide spectral range, such as a wide band of colors, and thus the eye sees an average effect over many wavelengths. The present invention proposes to solve this problem by illuminating the tissue of interest, such as a tissue that may be subsequently operated upon, with a surgical lamp according to the invention, such that the optical effects listed above may be enhanced. In particular the invention proposes a surgical lamp that can selectively emit light of different spectral compositions. For example, the first light source may emit light with a high Color Rendering Index which may be advantageous during normal operation of a surgical lamp and in the second light source may emit light with a dedicated spectral composition to enhance the above mentioned effects. It is understood that the invention is not about providing a diagnosis or about treating patients, however, embodiments of the invention may assist a physician in reaching a diagnosis or treating a patient.

The basic idea of the invention may be seen as illuminating associated animal tissues with light from a surgical lamp having a spectral composition, with strong components, such as emission peaks, within a spectral range where the illuminated objects have differing optical properties. Although the strong components may deteriorate the color rendering index of the surgical lamp, the contrast difference between the illuminated associated animal tissues may then be enhanced enabling an improved visually based discrimination between associated animal tissues. The light sources of the surgical lamp may be selectively turned on and off so that the color rendering index may also be high.

The color rendering index (CRI) (sometimes called color rendition index), is a quantitative measure of the ability of a light source to reproduce the colors of various objects faithfully in comparison with an ideal or natural light source. For some light sources the CRI cannot be calculated, because it is not possible to calculate a correlated color temperature (non-white light). In some embodiments the second light source is a white light source. In some other embodiments the second light source is non-white.

The first light source may comprise any type of light emitter, such as incandescent (halogen lamp or a tungsten filament), discharge lamp, LED or fluorescent light emitters. The first light source may comprise a number of first light emitters which number may be one or more than one.

The second light source may comprise a light emitting diode (LED), optionally equipped with spectral filters, or a LASER. The second light source may further comprise a spectral filter, so as to assist or enable the emission of light in the second spectral range. The LED may be an organic or inorganic LED. The second light source may comprise a number of second light emitters which number may be one or more than one. In one embodiment, there is provided a second light source which having a narrow emission peak and furthermore has an emission spectrum with a non-zero emission intensity outside the peak, such as a normal white light spectrum. A possible advantage of such embodiment is that the appearance of illuminated associated animal tissue remains somewhat normal, but contrast of certain types or states of tissue may still be enhanced. In another embodiment the second light source may have a zero, or close to zero background outside of the second emission peak. An advantage of this may be that contrast of certain tissue may appear more pronounced.

In another embodiment, there is provided a second light source which has a narrow emission peak within one or two of red, green, or blue spectral ranges corresponding to a sensitivity of the human eye, and which has normal white light distribution in the other colors. This has the advantage that the contrast is enhanced, but appearance remains normal for the other colors. This embodiment uses the effect that the human eye is separately sensitive for red, green and blue spectral ranges.

An advantage of having the first color rendering index being higher than the second color rendering index this may be that when illuminating using a light source with a high color rendering index, all colors are perceived correctly or close to correctly by the human eye, while when illuminating using a light source with a lower or non-definable color rendering index, certain objects may stand out. In an advantageous embodiment, an object of interest stands out, so as to be easily identified. In a further advantageous embodiment, the object which stands out is a tissue, of a certain type of state, such as a cancerous tissue. In a particular embodiment, the first light source of the surgical lamp may have a color rendering index (CRI) of 85-100, such as 90-100, such as 95-100. In another particular embodiment, the second light source of the surgical lamp may have a color rendering index (CRI) of less than 85, such as less than 70, such as less than 50, such as less than 20.

The surgical lamp may be a lamp suited for placing in the vicinity of an object to be illuminated, so as to enable sufficient light for the human eye to see the object clearly. The first light source and/or the second light source of the surgical lamp may have a central illuminance (this is the illuminance at 1000 mm distance) in the range of 40.000-160.000 lux. The first light source and/or the second light source of the surgical lamp may have a color temperature of 3000-6700 K. The first light source and/or the second light source of the surgical lamp may have a maximum value for total irradiance of maximum 1000 Watts per square meter. The first light source and/or the second light source of the surgical lamp may have a UV irradiance below 10 Watts per square meter. In a particular embodiment, the surgical lamp is further provided with a backup device, so that in case of interruption of the power supply, the light should be restored within 5 seconds with at least 50% of the previous lux intensity, but not less than 40 000 lux and in a further embodiment the light should within 40 seconds be restored, such as completely restored, to the original amount of lux. In a particular embodiment the first light source and/or the second light source of the surgical lamp has a depth of illumination, given as the distance under the light emitting area where the illumination reaches 60% of the central illuminance, which depth of illumination is large enough, such as at least 100 mm, such as at least 200 mm, such as at least 500 mm, such as at least 700 mm, so as to ensure that need for refocusing during an operation is minimized. In a particular embodiment the first light source and/or the second light source of the surgical lamp has a light field diameter being a diameter around a point in the lighted area where illuminance reaches maximum lux intensity, the light field diameter being of a size sufficiently large, such as 500 mm, such as 300 mm, such as 200 mm, such as 150 mm, such as 100 mm, such as 50 mm, so as to allow operations, such as surgical operations on a person or animal.

The first spectral range is associated with a CRI, and in some embodiments the CRI should be as high as possible and may therefore cover the entire visible spectral range, such as in a range from 380 to 780, such as in a range from 400 to 750 nm.

The second spectral range is a narrow spectral range with respect to the first spectral range and it is understood that the second spectral range may have a width, such as the full width at half maximum (FWHM) of the emission peak. There may also be a combination of peaks having a narrow spectral range (for example 2, 5, or 10 emission peaks). In particular embodiments, the width of the second spectral range may be less than 100 nm, such as less than 10 nm, such as less than 5 nm, such as less than 2 nm, such as less than 1 nm. In other particular embodiments, the width of the second spectral range may be larger than 100 nm, such as larger than 10 nm, such as larger than 5 nm, such as larger than 2 nm, such as larger than 1 nm. The embodiments may be combined so as to obtain embodiments where the width of the second spectral range may be, for example, in the range 1 nm-100 nm, such as in the range 10 nm-100 nm. The width of the second spectral range may also correspond to the width of the emission peak of the second light source used, such as the width of an emission peak of a mono-color LED, such as 15 nm, or the width of an emission peak of a LASER, such as <1 nm.

In another embodiment according to the invention a surgical lamp is provided, wherein the second spectral range at least partially overlaps with a spectral range of a an absorption peak in an associated animal tissue. An absorption peak of an associated animal tissue is in the present context understood to be a peak in an absorption spectrum of an associated animal tissue. Furthermore, in the present context, an absorption peak may also be understood to encompass a peak in differences between absorption spectra for different associated animal tissues, such as animal tissues of different type or state. A possible advantage of this may be that the associated animal tissue may visually stand out, due to its specific optical properties in the second spectral range when illuminated with the second light source of the surgical lamp. Another possible advantage is that it may be possible to create a visible contrast between the specific tissue type and other human or animal tissue types or states. In a particular embodiment, the second spectral range may have a width which is similar to the width of the absorption peak in the associated animal tissue, such as the width of the second spectral range being a percentage of the width of the absorption peak in the associated animal tissue, such as the percentage being in the range 1%-400%, such as the percentage being in the range 20%-300%, such as the percentage being in the range 50%-200%. It is understood that associated animal tissue is not a feature of the claim. It is generally understood that when referring to different tissues, such as different animal tissues, a tissue may differ in type and/or state, where state may, for example, refer to benign or malignant. When referring to animal tissue it is understood also to include human tissue.

In a further embodiment, a surgical lamp is provided wherein the second spectral range at least partially overlaps with a spectral range of a an absorption peak in an associated animal tissue and wherein the second spectral range comprises a wavelength, which wavelength is being chosen from the group comprising: 420 nm, 480 nm, and 550 nm. The wavelengths in this group corresponds to absorption peaks in animal tissues, such as 420 nm is indicative of Soret band hemoglobin levels, 480 nm is indicative of beta-carotene levels, and 550 nm is indicative of Q-band hemoglobin levels. An advantage may be that the second light source of the surgical lamp may be used to enhance a visible contrast between the specific tissue type state and other animal tissue types or states. In a further embodiment, the absorption peak corresponds to a spectral range comprising a wavelength chosen from the group comprising: 420 nm, 480 nm, and 550 nm. In yet another further embodiment, the emission peak is centered around a wavelength chosen from the group comprising: 420 nm, 480 nm, and 550 nm.

In another embodiment a surgical lamp is provided, wherein the spectral range of the absorption peak in the associated animal tissue is wider than the second spectral range. An advantage of this may be that light of the second light source is then emitted in a range not broader than the spectral range of the absorption peak, so as to avoid that the human eye of the observer sees an average effect over many wavelengths, which may diminish the effect.

In another embodiment a surgical lamp is provided wherein a maximum of the emission peak of the second light source is within the spectral range of the absorption peak in the associated animal tissue. An advantage of this may be, that the wavelengths where the intensity of light in the emission peak of the second light source is most intense coincides with the spectral range of the absorption peak such that the associated animal tissue may be more clearly discriminated with respect to other tissues.

In another embodiment there is provided a surgical lamp wherein a maximum of the absorption peak of the associated animal tissue is comprised within the second spectral range. This may be advantageous, for example, when the absorption peak of the associated animal tissue is wider than the second spectral range, since the emission peak of the second light source then coincides with the wavelength where the absorption peak of the associated animal tissue is most prominent.

In another embodiment according to the invention a surgical lamp is provided, wherein the second spectral range is comprised within a spectral range of an absorption peak in an associated animal tissue. This may for instance be advantageous if the second spectral range is very narrow compared to a width of the absorption peak of the associated animal tissue. An advantage of this may be, that the wavelengths where the intensity of light in the emission peak of the second light source is most intense coincides with the spectral range of the absorption peak such that the associated animal tissue may be more clearly discriminated with respect to other tissues.

In another embodiment according to the invention a surgical lamp is provided, wherein the first and second light source of the surgical lamp are arranged to emit light in a spatially distributed manner so as to enable shadow dilution. The spatially distributed emission of light may be achieved in various manners, such as using reflecting units, and or using a plurality of spatially distributed light emitters. The surgical lamp may enable shadow dilution, so that an object between the surgical lamp and the object to be illuminated does not necessarily cast a shadow on the object to be illuminated, which shadow may make it difficult for the human eye to see the object to be illuminated clearly.

In another embodiment according to the invention a surgical lamp is provided, wherein the second light source comprises a second light emitter capable of emitting light in a spectral range being broader than the second spectral range, and wherein the second light source further comprises a spectral filter, which spectral filter transmits light within a spectral range corresponding to the second spectral range. A possible advantage of this may be that the second spectral range may then be changed by changing the spectral filter. Another possible advantage may be that the spectral filter can allow transmission and thus emission of a relatively narrow spectral range, and that the embodiment may enable that the second light emitter to be of a low-cost type compared to other alternatives. It is also understood to be encompassed by the invention to have a single light emitter or a single type of light emitter, and change its emission spectrum using a spectral filter, so as to provide a first light source and a second light source, the first and the second light source differing in spectral filter properties. In a particular embodiment, a light emitter which emits white light of high CRI is used as first light source, and the second light source is the same light emitter and a spectral filter.

In another embodiment according to the invention a surgical lamp is provided, wherein the second light source comprises a second light emitter capable of emitting light having an emission peak in a spectral range corresponding to the second spectral range. A possible advantage of this may be that a spectral filter may not be needed. Another possible advantage may be that energy is not used to emit light in spectral regions besides in the second spectral range.

In another embodiment according to the invention a surgical lamp is provided, wherein the second light source comprises a second light emitter, which second light emitter is being chosen from the group comprising: a light emitting diode, a LASER. A possible advantage is that LEDs and especially LASERs can emit in a very narrow spectral range.

In another embodiment according to the invention a surgical lamp is provided, wherein the light emitted from the second light source comprises a plurality of separated emission peaks in a plurality of second spectral ranges, each second spectral range in the plurality of second spectral ranges being a narrow spectral range with respect to the first spectral range. In one embodiment, the second light source comprises a light emitter capable of emitting light in the plurality of separated emission peaks in the plurality of second spectral ranges.

In another embodiment according to the invention a surgical lamp is provided, the surgical lamp comprising a plurality of second light sources, each second light source in the plurality of second light sources being capable of emitting light having a separated emission peak, so that the plurality of second light sources is capable of emitting light in a plurality of separated emission peaks in a plurality of second spectral ranges, each second spectral range in the plurality of second spectral ranges being a narrow spectral range with respect to the first spectral range. An advantage of this may be, that turning second light sources in the plurality of second light sources on and off may relatively easily yield control over the spectrum of the emitted light. Another advantage may be that energy may be saved by turning off the second light sources which are emitting in second spectral ranges which are not used in a given period of time.

In a further embodiment according to the invention a surgical lamp is provided, wherein the surgical lamp is capable of selectively emitting light comprising any one of the plurality of separated emission peaks. An advantage of being capable of selectively emitting light comprising any one of the plurality of separated emission peaks may be that the surgical lamp may be applicable for different objects, with different optical properties, such as different animal tissues.

In another further embodiment according to the invention a surgical lamp is provided, wherein the surgical lamp is capable of simultaneously and selectively emitting light comprising two or more of the plurality of separated emission peaks. A possible advantage of this may be that the combination of several second spectral ranges, such as simultaneous emission of light in the several second spectral ranges, can improve the contrast between different tissues further.

According to a second aspect of the invention, there is presented a method for enabling improved visually based discrimination between associated animal tissues, the method comprising the steps of providing a surgical lamp according to claim 1, illuminating an associated animal tissue with the surgical lamp, and switching the second light source on or off so as to enable improved visually based discrimination between the associated animal tissue and another associated animal tissue, such as to generate a visible contrast.

None of the method steps require involvement of a medical practitioner. In one embodiment the method may be enabling the visually based discrimination between the associated animal tissues by generating a visible contrast for a human observer.

According to a third aspect of the invention, there is presented a use of a surgical lamp according to the first aspect, for illuminating an associated animal tissue.

The first, second and third aspects of the present invention may each be combined with any of the other aspects. These and other aspects of the invention will be apparent from and elucidated with reference to the embodiments described hereinafter.

BRIEF DESCRIPTION OF THE FIGURES

The surgical lamp according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
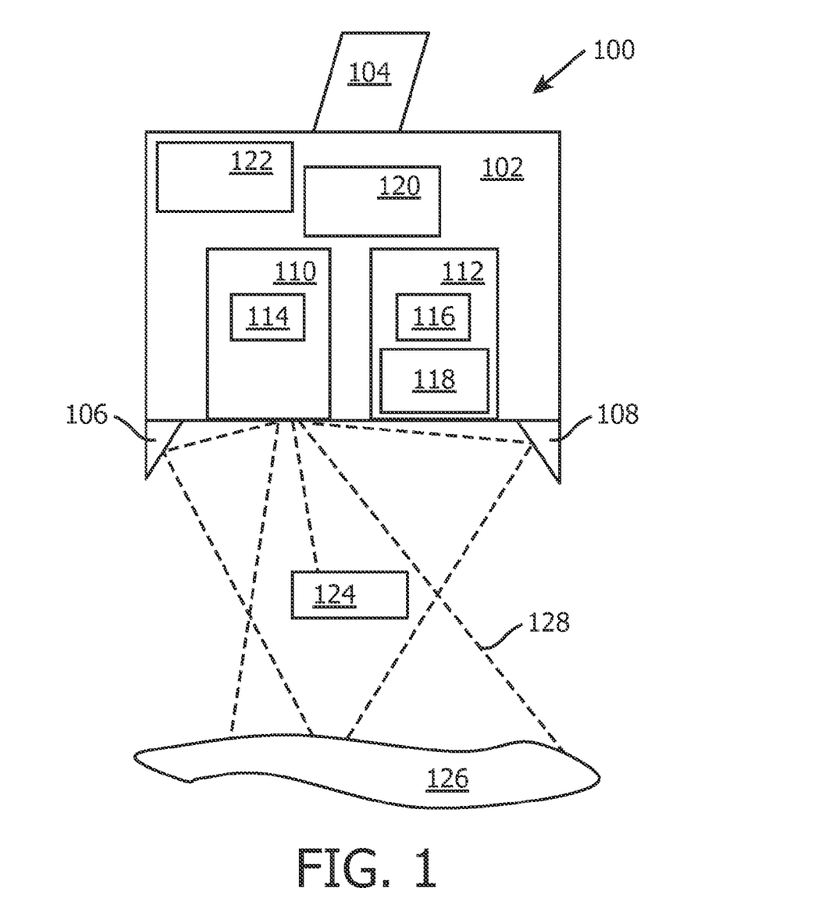
FIG. 1 shows a schematic illustration of a surgical lamp.

FIG. 1 shows a schematic illustration of a surgical lamp 100 where the surgical lamp comprises a casing 102. The surgical lamp further comprises a support arm 104, which holds the casing. The support arm may be attached to a ceiling, a wall, or a stand positioned on a floor. The support arm may provide a full range of movement while remaining stable once positioned. The surgical lamp 100 also comprises a first light source 110 with a first light emitter 114 and a second light source 112 with a second light emitter 116. In the shown embodiment, the second light 112 source also comprises a spectral filter 118. The spectral filter may be beneficial for allowing light to pass only in a narrow second spectral range. Furthermore, the surgical lamp 100 comprises a light source selecting device 120 for being capable of selectively switching the first light source on and off and further capable of selectively switching the second light source on and off. In a further embodiment, the light source selecting device may further be capable of other functions, such as selectively dimming each light source. The shown embodiment also features an input device 122, which input device may be beneficial for communicating from a user or an associated device to the light source selecting device 120 that it may be beneficial to turn a light source on or off. The input device 122 may be a manually operated device, such as a knob, a button, a toggle switch. In other embodiments, the input device may comprise a receiver for receiving electrical signals or wireless signals, such as infrared signals or radio frequency (RF) signals. The shown surgical lamp 104 also has reflecting units 106, 108 which are arranged for reflecting light from the first light source and/or the second light source towards a region of interest, so that a number of individual rays of light may be generated. In FIG. 1 the first light source emits light, which light is indicated as dotted lines 128, and some of the light is reflected of reflecting units 106, 108. An advantage of having light reflected towards a region of interest may be that more light is thus emitted towards the region of interest. Another advantage may be that the light arriving at the region of interest is arriving from a number of spatially distributed points, such as the first light source 110, reflecting unit 106 and reflecting unit 108. An advantage of having light arriving from a number of spatially distributed points may be that an object 124 in the direct line of sight between first light source 110 and an associated animal tissue 126, is less likely to cause a shadow on the associated animal tissue 126. This effect may be referred to as shadow dilution.

Figure 2:
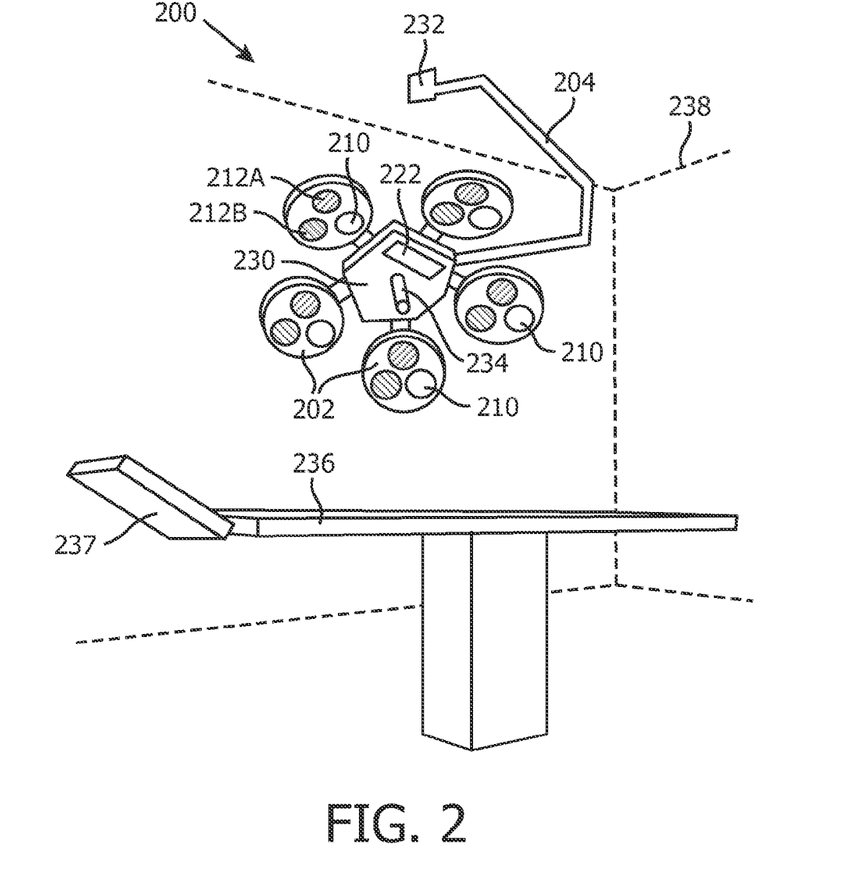
FIG. 2 shows a perspective drawing of a surgical lamp.

FIG. 2 shows a perspective drawing of a surgical lamp 200. The surgical lamp 200 is shown in an operating room, where the borders between walls, floor and ceiling are shown with dotted lines 238. FIG. 2 also shows an operating table 236 with a headrest 237. The surgical lamp 200 is shown mounted in the ceiling with a ceiling mounting plate 232 and movably suspended in a support arm 204. The surgical lamp 200 in FIG. 2 comprises spatially distributed 5 casings 202, each casing comprising a first light source 210 being capable of emitting light in a first spectral range, and two second light sources 212A-B, where the two second light sources 212A-B are each capable of emitting light having a separated emission peak with respect to the other, so that the two second light sources are capable of emitting light in two separated emission peaks in two second spectral ranges, each second spectral range being a narrow spectral range with respect to the first spectral range. As the casings 202 are spatially distributed, so is the plurality of first and second light sources. As opposed to the embodiment shown in FIG. 1, the present embodiment thus achieves spatial distribution of the individual light rays not by reflecting units, but by spatially distributing the first and second light sources. Again, an advantage may be that shadow dilution may be achieved, so that an opaque object, such as a hand or a head, between the surgical lamp and another object on the operating table 236 is less likely to cast a shadow on the object on the operating table. The surgical lamp 200 has a middle casing 230 whereupon is placed a position handle 234 and an input device 222, which input device comprises buttons and knobs so as to enable a user to manually turn on and off the first and/or second light source, and furthermore control other functions such as dimming the first and/or second light source. In the embodiment depicted in FIG. 2 the first and second light sources have their own optics for forming the light beam. However, in other embodiments the optics may be shared for the first and second light sources. As an example of shared optical elements, the reflecting units 106, 108 shown in FIG. 1 on a single casing may be shared between the first and the second light source.

Figure 3:
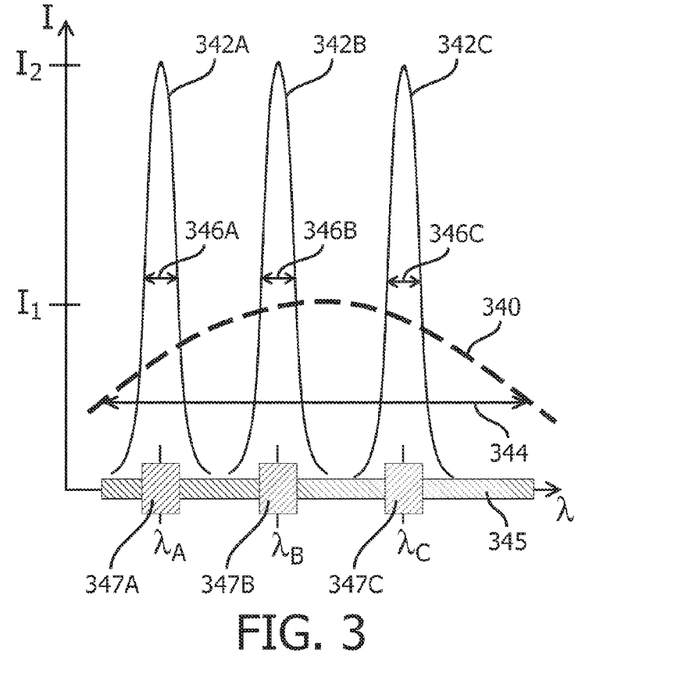
FIG. 3 is a schematic spectrum showing emission peaks.

FIG. 3 is an exemplary spectrum showing emission peaks. The figure shows a graph with intensity I on the vertical axis and wavelength λ (lambda) on the horizontal axis.

In the graph is shown an emission peak of first light source 340 with amplitude I_1, emission peaks of second light source(s) 342A-C with amplitude I_2 and placed, respectively on $\lambda_A$ (lambda_A), $\lambda_B$ (lambda_B) and $\lambda_C$ (lambda_C). The emission peak of the first light source is shown with a width 344, such as the full width at half maximum (FWHM). Furthermore is shown a first spectral range 345 is indicated on the horizontal axis and FWHMs of emission peaks of first light source(s) 346A-C and second spectral ranges 347A-C. In FIG. 3 the emission peaks of second light source(s) 342A-C are shown with similar widths 346A-C and amplitudes I_1, however, it may also be the case that only some of the emission peaks if the second light source(s) are similar in terms of width and/or amplitude or that no emission peaks of the second light source(s) are similar in terms of width and/or amplitude.

Figure 4:
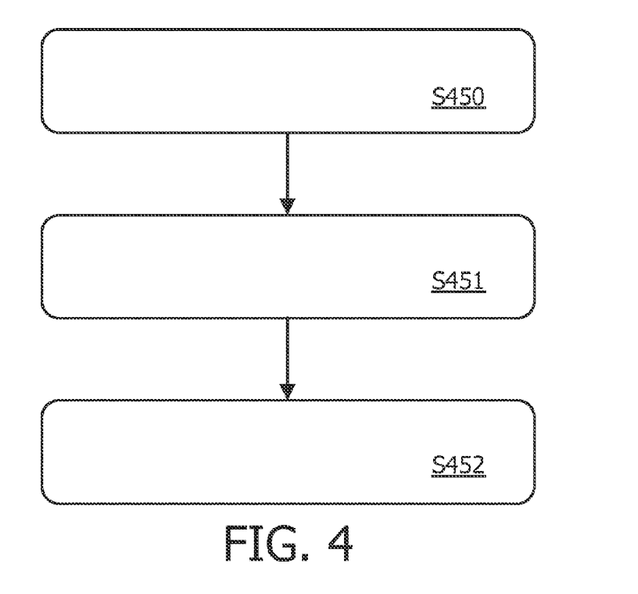
FIG. 4 is a flow-chart of a method according to the invention.

FIG. 4 is a flow-chart of a method according to the invention, which method is a method for enabling improved visually based discrimination between associated animal tissues, the method comprising the steps of providing S450 a surgical lamp as described above in connection with FIG. 1, illuminating S451 an associated animal tissue with the surgical lamp, and switching S452 the second light source on or off so as to enable improved visually based discrimination between the associated animal tissue and another associated animal tissue.

Figure 5A:
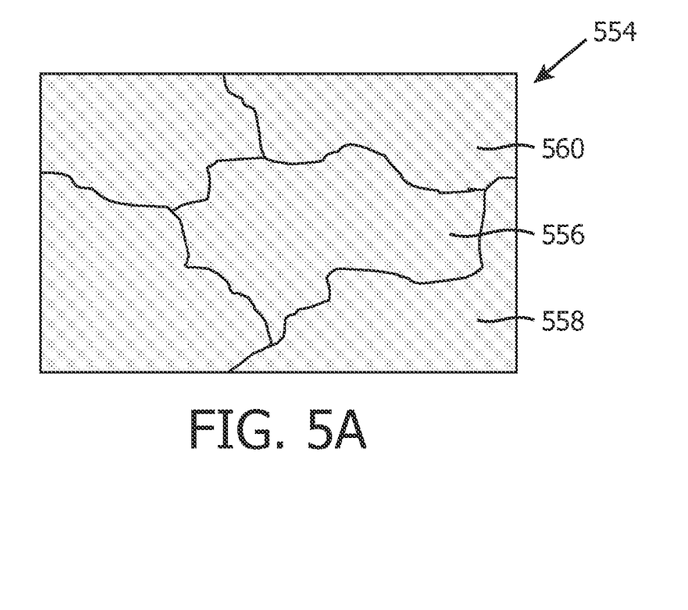
FIG. 5 is an explanatory view schematically illustrating a region of interest with a number of tissues under different illumination conditions.
Figure 5B:
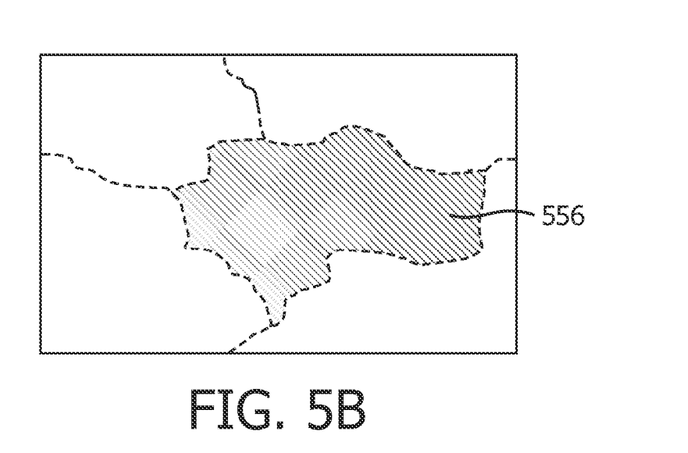

FIG. 5 is an explanatory view schematically illustrating a region of interest (ROI) 554 with a number of animal tissues as observed by a human eye under different illumination conditions. The animal tissues include an animal tissue of interest 556 placed centrally in the ROI, and a number of other animal tissues 558, 560 placed peripherally in the ROI. FIG. 5A shows the ROI under illumination with a surgical lamp according to an embodiment of the invention where the ROI is illuminated with the first light source of the surgical lamp, all non-transparent animal tissues are clearly visible and appear in their true color, although still not easily distinguishable. FIG. 5B shows the ROI under illumination with the second light source of the surgical lamp according to an embodiment of the invention where in the present embodiment the light has an emission peak in a second spectral range which is comprised in a spectral range of an absorption peak in the animal tissue of interest 556. Although the color rendering index (CRI) of the second light source is relatively low, the animal tissue of interest 556 now appears more distinguishable from the other animal tissues 558, 560. Notice that FIG. 5 is a stylistic representation of an effect which may be achieved with embodiment according to the invention, however, the effect may also be more subtle, for example where the tissue of interest 556 becomes darker or lighter, or the other tissues 558, 560 becomes darker or lighter. In practice also more colors may be involved, so instead of changing the appearance of different tissues to darker or lighter, the appearance may also be changed in terms of perceived color.

Figure 6:
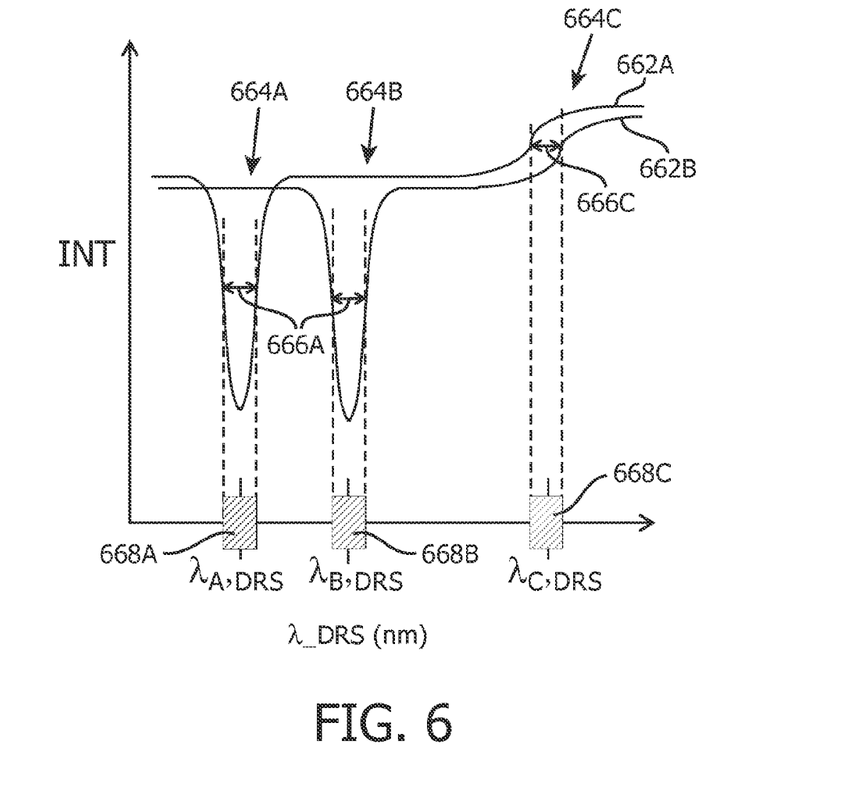
FIG. 6 is a schematic drawing of Diffuse Reflectance Spectra for two different animal tissues.

FIG. 6 is a schematic drawing of Diffuse Reflectance Spectra for two different animal tissues. The vertical axis shows intensity INT on the vertical axis and wavelength λ_DRS on the horizontal axis. The two different curves 662A, 662B represent different tissues which may differ in type or state, such as, for example, one being a malignant tissue and the other being a benign tissue. The two curves differ in their optical properties in three different wavelength regions, corresponding to spectral ranges 668A-C. The curve 662A has an absorption peak 664A at wavelength $\lambda_{A,DRS}$ and with a width 666A. The curve 662B has an absorption peak 664B at another wavelength $\lambda_{B,DRS}$ and with a width 666B. The two tissues of the two spectra differ in the spectral ranges 668A, 668B of the absorption peaks. Furthermore, although none of the spectra have an absorption peak at a position 664C in the right hand side, the difference in their absorption may differ. Furthermore, the difference in absorption between the two spectra 662A-B, may be a peak with a width 666C at a wavelength $\lambda_{C,DRS}$ in a spectral range 668C. An example of a measured Diffuse Reflectance Spectra can be found in the research paper "The Optical Biopsy Pill", Til Dallavalle et al., New York State Science and Technology Law Center at Syracuse University College of Law, dated Mar. 31, 2006 (publicly available on the internet page http://www.medisciencetech.com/append/OpticalBiopsyPill.htm on 29 Jul. 2010) which is hereby included by reference in its entirety, and in particular reference is made to FIG. 3.2.4.a and corresponding text in the reference.

Figure Annotations for Reference Signs
100 surgical lamp
102 casing
104 support arm
106 reflecting unit
108 reflecting unit
110 first light source
112 second light source
114 first light emitter
116 second light emitter
118 spectral filter
120 light source selecting device
122 input device
124 object
126 an associated animal tissue
128 light
200 surgical lamp
202 casing
204 support arm
210 first light source
212A second light source
212B second light source
222 input device
230 central part of surgical lamp
232 ceiling mounting plate
234 position handle
236 operating table
237 headrest
238 border between wall/wall, wall/ceiling or wall/floor
340 emission peak of first light source
342A-C emission peaks of second light source(s)
344 FWHM of emission peak of first light source
345 first spectral range
346A-C FWHMs of emission peaks of first light source(s)
347A-C second spectral ranges
S450 providing a surgical lamp according to claim 1,
S451 illuminating an associated animal tissue
S452 switching between the first light source and the second light source
554 a region of interest (ROI)
556 animal tissue of interest
558 animal tissue 560 animal tissue
662A-B DRS spectra
664A-B absorption peaks
664C region with peak in difference between spectra
666A-B widths of peaks
666C width of peak in difference spectrum
668A-C spectral ranges To sum up the present invention relates to a surgical lamp (100) comprising both a first light source (110) and a second light source (112), where the first light source is capable of emitting light across a broad first spectral range and the second light source being capable of emitting light having an emission peak in a narrow second spectral range. The surgical lamp further features a light source selecting device (120), capable of selectively turning on and off the first and the second light source. The first light source has a high color rendering index so as to enable objects, such as tissues, to appear in their true color, and the second light source has a low or non-definable color rendering index, so as enable accentuation of particular tissues.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A surgical lamp (100) comprising
a first light source (110), the first light source being capable of emitting light across a first spectral range (345), and
a second light source (112), the second light source being capable of emitting light having an emission peak (342A), which emission peak has a width (346A) corresponding to a second spectral range (347A),
wherein the second spectral range is a narrow spectral range with respect to the first spectral range and wherein the first light source (110) has a definable first color rendering index and the second light source (112) has a definable second color rendering index being lower than the first color rendering index or the second light source has a second color rendering index being non-definable, the surgical lamp further comprising
a light source selecting device (120),
where the light source selecting device is capable of selectively switching the first light source on and off and further capable of selectively switching the second light source on and off,
wherein the first and second light sources of the surgical lamp are arranged to emit light (128) in a spatially distributed manner so as to enable shadow dilution,
wherein the light emitted from the second light source (112) comprises a plurality of separated emission peaks in a plurality of second spectral ranges (347A, 347B, 347C), each second spectral range in the plurality of second spectral ranges being a narrow spectral range with respect to the first spectral range (345).

2. A surgical lamp according to claim 1, wherein the second spectral range (347A) at least partially overlaps with a spectral range of an absorption peak in an associated animal tissue.

3. A surgical lamp according to claim 2, wherein the second spectral range (347A) comprises a wavelength, which wavelength is being chosen from the group comprising: 420 nm, 480 nm, and 550 nm.

4. A surgical lamp according to claim 1, wherein a maximum of the emission peak of the second light source is within the spectral range of the absorption peak in the associated animal tissue.

5. A surgical lamp according to claim 1, wherein a maximum of the absorption peak of the associated animal tissue is comprised within the second spectral range.

6. A surgical lamp according to claim 1, wherein the second spectral range (347A) is comprised within a spectral range of an absorption peak in an associated animal tissue.

7. A surgical lamp according to claim 1, wherein the second light source (112) further comprises a second light emitter (116) capable of emitting light in a spectral range being broader than the second spectral range (347A), and wherein the second light source further comprises a spectral filter (118), which spectral filter transmits light within a spectral range corresponding to the second spectral range.

8. A surgical lamp according to claim 1, wherein the second light source (112) comprises a second light emitter (116), which second light emitter is being chosen from the group comprising: a light emitting diode, a LASER.

9. A surgical lamp (100) comprising
a first light source (110), the first light source being capable of emitting light across a first spectral range (345), and
a plurality of second light sources (112). the second light sources being capable of emitting light having an emission peak (342A), which emission peak has a width (346A) corresponding to a second spectral range (347A),
wherein the second spectral range is a narrow spectral range with respect to the first spectral range and wherein the first light source (110) has a definable first color rendering index and the second light source (112) has a definable second color rendering index being lower than the first color rendering index or the second light source has a second color rendering index being non-definable, the surgical lamp further comprising
a light source selecting device (120),
where the light source selecting device is capable of selectively switching the first light source on and off and further capable of selectively switching the second light source on and off,
wherein the first and second light sources of the surgical lamp are arranged to emit light (128) in a spatially distributed manner so as to enable shadow dilution, the surgical lamp (100) comprising a plurality of second light sources,
wherein each second light source in the plurality of second light sources being capable of emitting light having a separated emission peak, so that the plurality of second light sources is capable of emitting light in a plurality of separated emission peaks in a plurality of second spectral ranges (347A, 347B, 347C), each second spectral range in the plurality of second spectral ranges being a narrow spectral range with respect to the first spectral range (345).

10. A surgical lamp according to claim 9, wherein the surgical lamp (100) is capable of selectively emitting light comprising any one of the plurality of separated emission peaks (342A, 342B, 342C).

11. A surgical lamp according to claim 9, wherein the surgical lamp (100) is capable of simultaneously and selectively emitting light comprising two or more of the plurality of separated emission peaks (342A, 342B, 342C).

12. A method for enabling improved visually based discrimination between associated animal tissues, the method comprising the steps of
   providing (S450) a surgical lamp wherein the surgical lamp includes,
      a first light source (110), the first light source being capable of emitting light across a first spectral range (345), and
      a second light source (112), the second light source being capable of emitting light having an emission peak (342A), which emission peak has a width (346A) corresponding to a second spectral range (347A),
      wherein the second spectral range is a narrow spectral range with respect to the first spectral range and wherein the first light source (110) has a definable first color rendering index and the second light source (112) has a definable second color rendering index being lower than the first color rendering index or the second light source has a second color rendering index being non-definable, the surgical lamp further comprising
      a light source selecting device (120),
      where the light source selecting device is capable of selectively switching the first light source on and off and further capable of selectively switching the second light source on and off,
      wherein the first and second light sources of the surgical lamp are arranged to emit light (128) in a spatially distributed manner so as to enable shadow dilution,
      wherein the light emitted from the second light source (112) comprises a plurality of separated emission peaks in a plurality of second spectral ranges (347A, 347B, 347C), each second spectral range in the plurality of second spectral ranges being a narrow spectral range with respect to the first spectral range (345),
   illuminating (S451) an associated animal tissue with the surgical lamp, and
   switching (S452) the second light source on or off so as to enable improved visually based discrimination between the associated animal tissue and another associated animal tissue.

* * * * *